(12) United States Patent
Brookhart et al.

(10) Patent No.: US 7,034,093 B2
(45) Date of Patent: Apr. 25, 2006

(54) CATALYSTS FOR OLEFIN POLYMERIZATION

(75) Inventors: Maurice S. Brookhart, Chapel Hill, NC (US); Olafs Daugulis, Carrboro, NC (US)

(73) Assignees: E. I. du Pont de Nemours and Company, Wilmington, DE (US); University of North Carolina, Chapel Hill, NC (US)

( * ) Notice: Subject to any disclaimer, the term of this patent is extended or adjusted under 35 U.S.C. 154(b) by 21 days.

(21) Appl. No.: 10/501,132

(22) PCT Filed: Mar. 5, 2003

(86) PCT No.: PCT/US03/06817

§ 371 (c)(1),
(2), (4) Date: Jul. 9, 2004

(87) PCT Pub. No.: WO03/078478

PCT Pub. Date: Sep. 25, 2003

(65) Prior Publication Data

US 2005/0119429 A1 Jun. 2, 2005

Related U.S. Application Data

(60) Provisional application No. 60/362,044, filed on Mar. 6, 2002.

(51) Int. Cl.
*C08F 4/70* (2006.01)
*C07F 9/50* (2006.01)
*C07F 15/04* (2006.01)

(52) U.S. Cl. ............... 526/172; 526/161; 526/165; 526/169.1; 526/348; 526/352; 564/248; 568/17; 556/21; 556/32

(58) Field of Classification Search ......... 526/172, 526/161, 165, 169.1, 348, 352; 568/17; 556/21, 556/32; 564/248
See application file for complete search history.

(56) References Cited

U.S. PATENT DOCUMENTS 5,955,555 A 9/1999 Bennett
6,423,794 B1 * 7/2002 Guan ............... 526/139

FOREIGN PATENT DOCUMENTS

WO  WO 98/40420  9/1998
WO  WO 00/59956  10/2000

* cited by examiner

*Primary Examiner*—Caixia Lu

(57) ABSTRACT

Late transition metal complexes of certain neutral iminophosphine ligands are useful as components of polymerization catalysts for olefins. Useful metals in the complexes include Ni, Pd, Fe and Co. Oligomers and/or polymers of olefins such as ethylene can be made.

15 Claims, No Drawings

CATALYSTS FOR OLEFIN POLYMERIZATION

The application claims the benefit of Provisional application No. 60/362,044, filed Mar. 6, 2002.

FIELD OF THE INVENTION

New late transition metal complexes with neutral iminophosphine ligands useful as catalyst components in the polymerization of olefins, such as ethylene, are described.

TECHNICAL BACKGROUND

The (co)polymerization of olefins, especially olefins such as ethylene and propylene by themselves or with other olefins is one of largest parts of the worldwide chemical industry. The resulting polymer are in a myriad of ways, and therefore new methods of polymerizing these monomers and/or finding polyolefins with new and different structures are always of interest. Recently it was discovered that certain complexes of late transition metals could be used as part of polymerization catalyst systems for these olefins. Some of these catalyst systems produced polymers with unique structures.

World Patent Applications 00/59956 and 98/40420, describe the use of certain late transition metal complexes of iminophosphines as components of olefin polymerization catalysts. None of the ligands and complexes described herein is specifically described in these references.

SUMMARY OF THE INVENTION

This invention concerns a process for the polymerization of olefins, comprising, using a polymerization catalyst system comprising a Ni, Pd, Fe or Co complex of a ligand of the formula

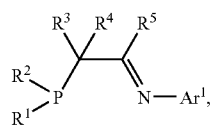

(I)

wherein:
 Ar$^1$ is aryl or substituted aryl;
 R$^1$ is hydrocarbyl, substituted hydrocarbyl, hydrocarbyloxy, or substituted hydrocarbyloxy;
 R$^2$ hydrocarbyl or substituted hydrocarbyl;
 R$^3$ and R$^4$ are each hydrocarbyl or substituted hydrocarbyl, or R$^3$ and R$^4$ taken together form a ring; and
 R$^5$ is hydrocarbyl or substituted hydrocarbyl.

Also disclosed herein is a compound of the formula

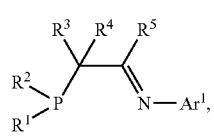

(I)

wherein:

Ar$^1$ is aryl or substituted aryl;
R$^1$ is hydrocarbyl, substituted hydrocarbyl, hydrocarbyloxy, or substituted hydrocarbyloxy;
R$^2$ hydrocarbyl or substituted hydrocarbyl;
R$^3$ and R$^4$ are each hydrocarbyl or substituted hydrocarbyl, or R$^3$ and R$^4$ taken together form a ring; and
R$^5$ is hydrocarbyl or substituted hydrocarbyl.

Another material disclosed herein is a transition metal complex of a compound of the formula

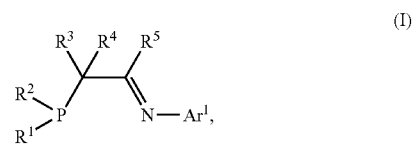

(I)

wherein:
 Ar$^1$ is aryl or substituted aryl;
 R$^1$ is hydrocarbyl, substituted hydrocarbyl, hydrocarbyloxy, or substituted hydrocarbyloxy;
 R$^2$ hydrocarbyl or substituted hydrocarbyl;
 R$^3$ and R$^4$ are each hydrocarbyl or substituted hydrocarbyl, or R$^3$ and R$^4$ taken together form a ring; and
 R$^5$ is hydrocarbyl or substituted hydrocarbyl.
 and wherein said transition metal is Fe, Co, Ni or Pd.

DETAILS OF THE INVENTION

A "hydrocarbyl group" is a univalent group containing only carbon and hydrogen. If not otherwise stated, it is preferred that hydrocarbyl groups (and alkyl groups) herein contain 1 to about 30 carbon atoms.

A "hydrocarbyloxy group" is a univalent group containing carbon, hydrogen and one oxygen atom, and the free valence of the group is to that oxygen atom.

By "substituted hydrocarbyl(oxy)" herein is meant a hydrocarbyl(oxy) group that contains one or more substituent groups which are inert under the process conditions to which the compound containing these groups is subjected (e.g., an inert functional group, see below). The substituent groups also do not substantially detrimentally interfere with the polymerization process or operation of the polymerization catalyst system. If not otherwise stated, it is preferred that substituted hydrocarbyl(oxy) groups herein contain 1 to about 30 carbon atoms. Included in the meaning of "substituted" are chains or rings containing one or more heteroatoms, such as nitrogen, oxygen and/or sulfur, and the free valence of the substituted hydrocarbyl may be to the heteroatom. In a substituted hydrocarbyl, all of the hydrogens may be substituted, as in trifluoromethyl.

By "(inert) functional group" herein is meant a group other than hydrocarbyl or substituted hydrocarbyl that is inert under the process conditions to which the compound containing the group is subjected. The functional groups also do not substantially interfere with any process described herein that the compound in which they are present may take part in. Examples of functional groups include halo (fluoro, chloro, bromo and iodo), silyl, and ether such as —OR$^{22}$ wherein R$^{22}$ is hydrocarbyl or substituted hydrocarbyl. In cases in, which the functional group may be near a transition metal atom the functional group should not coordinate to the metal atom more strongly than the groups in those compounds are shown as coordinating to the metal atom, that is they should not displace the desired coordinating group.

By "silyl" herein is meant a monovalent group whose free valence is to a silicon atom. The other three valencies of the silicon atom are bound to other groups such as alkyl, halo, alkoxy, etc. Silyl groups are also included in functional groups.

By a "cocatalyst" or a "catalyst activator" is meant one or more compounds that react with a transition metal compound to form an activated catalyst species. One such catalyst activator is an "alkyl aluminum compound" which, herein, is meant a compound in which at least one alkyl group is bound to an aluminum atom. Other groups such as, for example, alkoxide, hydride and halogen may also be bound to aluminum atoms in the compound.

By "neutral Lewis acid" is meant a compound, which is not an ion, which can act as a Lewis acid. Examples of such compounds include boranes, alkylaluminum compounds, aluminum halides, and antimony [V] halides.

By an "empty coordination site" is meant a potential coordination site on a transition metal atom that does not have a ligand bound to it. Thus if an olefin molecule (such as ethylene) is in the proximity of the empty coordination site, the olefin molecule may coordinate to the metal atom.

By a "ligand into which an olefin molecule may insert between the ligand and a metal atom", or a "ligand that may add to an olefin", is meant a ligand coordinated to a metal atom which forms a bond (L-M) into which an olefin molecule (or a coordinated olefin molecule) may insert to start or continue a polymerization. For instance, with ethylene this may take the form of the reaction (wherein L is a ligand):

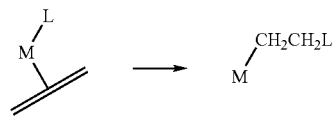

For a summary of which ligands ethylene may insert into (between the ligand and transition metal atom) see for instance J. P. Collman, et al., *Principles and Applications of Organotransition Metal Chemistry*, University Science Books, Mill Valley, Calif., 1987.

By relatively noncoordinating (or weakly coordinating) anions are meant those anions as are generally referred to in the art in this manner, and the coordinating ability of such anions is known and has been discussed in the literature, see for instance W. Beck., et al., *Chem. Rev.*, vol. 88 p. 1405–1421 (1988), and S. H. Stares, *Chem. Rev., vol.* 93, p. 927–942 (1993), both of which are hereby included by reference. Among such anions are those formed from the aluminum compounds in the immediately preceding paragraph and X$^-$, including R$^9_3$AlX$^-$, R$^9_2$AlClX$^-$, R$^9$AlCl$_2$X$^-$, and "R$^9$AlOX$^-$", wherein R$^9$ is alkyl. Other useful noncoordinating anions include BAF$^-${BAF=tetrakis[3,5-bis(trifluoromethyl)phenyl]borate}, SbF$_6^-$, PF$_6^-$, and BF$_4^-$, trifluoromethanesulfonate, p-toluenesulfonate, (R$_f$SO$_2$)$_2$N$^-$, and (C$_6$F$_5$)$_4$B$^-$.

By a "ligand which may be displaced by an olefin" is meant a ligand coordinated to a transition metal which, when exposed to the olefin (such as ethylene), is displaced as the ligand by the olefin.

By a "neutral ligand" is meant a ligand that is not charged.

"Alkyl group" and "substituted alkyl group" have their usual meaning (see above for substituted under substituted hydrocarbyl). Unless otherwise stated, alkyl groups and substituted alkyl groups preferably have 1 to about 30 carbon atoms.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

By "R$^x$ and R$^y$ taken together may form a double bond" is meant a structure originally written as —CRR$^x$—CRR$^y$— is, when R$^x$ and R$^y$ do in fact form a double bond, —CR=CR—. In this example each R is simply another group on a carbon atom to satisfy carbon's normal valence requirement of 4.

By a "π-allyl group" is meant a monoanionic ligand comprised of 1 sp$^3$ and two sp$^2$ carbon atoms bound to a metal center in a delocalized η$^3$ fashion indicated by

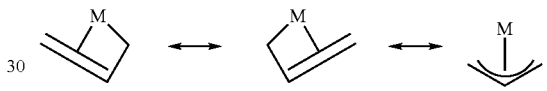

The three carbon atoms may be substituted with other hydrocarbyl groups or functional groups.

By a "hydrocarbon olefin" is meant an olefin containing only carbon and hydrogen.

By a "polar (co)monomer" or "polar olefin" is meant an olefin which contains one or more elements other than carbon and hydrogen. When copolymerized into a polymer the polymer is termed a "polar copolymer". Useful polar comonomers are found in U.S. Pat. No. 5,866,663, WO 9905189, WO 9909078 and WO 9837110, and S. D. Ittel, et al., *Chem. Rev.*, vol. 100, p. 1169–1203(2000), all of which are incorporated by reference herein for all purposes as if fully set forth. Also included as a polar comonomer is CO (carbon monoxide).

In the transition metal complexes described herein (I) to a transition metal atom. (I), as shown by the above formulas, is a neutral ligands usually only one molecule of (I) is coordinated to the transition metal atom. The other coordination sites of the metal atom are usually occupied by other ligands (see below), but one of these coordination sites may be empty. Preferred transition metals are Ni and Pd, and Ni is especially preferred.

One type of preferred monomer are hydrocarbon monomers, such as ethylene and α-olefins of the formula H$_2$C=CH—(CH$_2$)$_m$CH$_3$ wherein m is 0 (propylene) or an integer of 1 to about 20). A preferred monomer is ethylene, or to make a copolymer ethylene and one or more α-olefins. Another type of preferred polymer is a copolymer of ethylene and a polar comonomer (see above). Preferably the polar comonomer is one or both of an acrylate ester and a vinylsilane. Other useful types of monomers include styrenes, norbornenes, and cyclopentenes.

By "polymerization" herein is meant at least two olefin molecules are combined into a single molecule ("dimerized"), or an oligomer or polymer is formed. Preferably the average degree of polymerization (DP, the average number of monomer units in the product molecules) is 5 or more, more preferably about 10 more, and especially preferably about 25 or more. When "dimers" or other low oligomers are made they often contain branching (often 1 branch) and/or an internal olefin.

For all purposes herein (both processes and compositions) preferred groups and structures for (I) are:

- $Ar^1$ is phenyl or substituted phenyl, more preferably substituted phenyl, and especially preferably 2,2,6, or 2,4,6 substituted phenyl, wherein in any of these substituted phenyl groups alkyl groups containing 1–4 carbon atoms are preferred substituents;
- $R^1$ is alkyl, substituted alkyl, aryl, substituted aryl, aryloxy, or substituted aryloxy, more preferably alkyl, phenyl, substituted phenyl, phenoxy and substituted phenoxy;
- $R^2$ is alkyl, substituted alkyl, aryl or substituted aryl, more preferably methyl, phenyl or substituted phenyl;
- $R^3$ and $R^4$ are each independently alkyl or substituted alkyl, more preferably both $R^3$ and $R^4$ are methyl; and
- $R^5$ is hydrogen, aryl, substituted aryl, alkyl or substituted alkyl.

Within all of the preferred forms of (I) above any combination of enumerated preferable groups may be chosen to form a preferred compound.

In the polymerization process involving transition metals complexes of (1), these complexes comprise part or all of a polymerization catalyst system. By comprises or comprising the polymerization catalyst system is meant the catalyst may consist of the metal complex and any other components needed or desired as part of the catalyst system. Depending on the nature of the other "parts" of the transition metal complex, the complex itself may be able, by itself, to cause polymerization of olefin(s), or other components such as one or more co-catalysts and/or activators may also be needed to cause polymerization. For example compounds such as C17 through C20 (see the Examples below) are by themselves "complete" polymerization catalyst systems. These complexes are characterized as having a relatively noncoordinating anion, and ligands which may be displaced by and/or insert an olefin such as ethylene. Such groups include π-allyl groups, acetonitrile (which can be displaced by an olefin), and methyl groups (into which an olefin can insert between the methyl group and the metal atom). Many of these types of compounds are well known. For example see analogous types of complexes with α-diimines in U.S. Pat. No. 5,880, 241, which is hereby included by reference.

However as mentioned above certain complexes require activators. For example, (see C21 through C26, below) one such type of complex may be

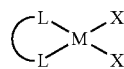

(IV)

wherein each X is a halide anion and

represents the ligand (I), which in fact may be bidentate. In order for (IV) to be catalytically active it needs to be converted to a complex which has at least one ligand to which an olefin group can add, and one ligand which can be displaced by an olefin or open coordination site to which an olefin may bind to the metal. This can be accomplished by adding to (IV) a compound which can alkylate the metal in (IV), i.e. convert X to alkyl, and which in addition a strong enough Lewis acid to abstract one of the alkyl groups from M to form a relatively noncoordinating anion and an empty coordination site on M. This can be done for example by reacting (IV) with an alkylaluminum compound. In actual polymerization processes this is often done in situ in the polymerization reactor itself, by adding (IV) and the alkylaluminum to the reactor. There are many other methods of activating transition metal complexes for use as olefin polymerization catalysts, see for example U.S. Pat. No. 5,880,241 which describes methods applicable to the complexes described herein.

During the polymerization itself certain compounds containing the transition metal complex and which are active in the polymerization, and which may be termed intermediates may also be formed. For example a compound of the formula

(V)

may be an active intermediate in the polymerization (in this case of ethylene). In (V) Z is a polymethylene chain of indeterminate length formed by the polymerization of ethylene, T was the original group on the complex into which ethylene could insert, X is a relatively noncoordinating anion, and

is an ethylene molecule. The ethylene molecule may insert in between M and Z thereby adding another monomer unit to the polymer chain, and another ethylene molecule may coordinate to M. This propagation cycle builds up the molecular weight of the polymer being formed. Analogous intermediates with other ligands (for example α-dimines) are found in U.S. Pat. No. 5,880,241, and (I) may be substituted for the α-dimines shown in structures in U.S. Pat. No. 5,880,241.

In the polymerization process herein, the temperature at which the polymerization is carried out is about −100° C. to about +200° C., preferably about −20° C. to about 120° C., more preferably about 0° C. to about 100° C. The pressure of the ethylene or other gaseous olefin at which the polymerization is carried out is not critical, atmospheric pressure to about 275 MPa being a suitable range.

The polymerization process herein may be run in the presence of various liquids, particularly aprotic organic liquids. The catalyst system, ethylene or other olefinic monomer, and/or polymer may be soluble or insoluble in these liquids, but obviously these liquids should not prevent the polymerization from occurring. Suitable liquids include alkanes, cycloalkanes, selected halogenated hydrocarbons, and aromatic hydrocarbons. Specific useful solvents include hexane, toluene, benzene, methylene chloride, 1,2,4-trichlorobenzene and p-xylene.

The polymerization process herein may also initially be carried out in the "solid state" by, for instance, supporting the transition metal compound on a substrate such as silica or alumina, activating if necessary it with one or more cocatalysts and contacting it with, say, ethylene. The support may be considered part of the polymerization catalyst system. Alternatively, the support may first be contacted (reacted) with a cocatalysts (if needed) such as an alkylaluminum compound, and then contacted with an appropriate transition metal compound. The support may also be able to take the place of a Lewis or Bronsted acid, for instance an acidic clay such as montmorillonite, if needed. These "heterogeneous" catalysts may be used to catalyze polymerization in the gas phase or the liquid phase. By gas phase is meant that a gaseous olefin is transported to contact with the catalyst particle. In a preferred form of gas phase polymerization the polymerization catalysts and/or polymer formed is in the form of a fluidized bed.

Depending on their properties, the polyolefins made by the processes described herein are useful in many ways. For instance if they are thermoplastics, they may be used as molding resins, for extrusion, films, etc. If they are elastomeric, they may be used as elastomers. If they contain functionalized monomers such as acrylate esters or other polar monomers, they are useful for other purposes, see for instance previously incorporated U.S. Pat. No. 5,880,241.

Depending on the polymerization process conditions used and the polymerization catalyst system chosen, the polyolefins may have varying properties. Some of the properties that may change are molecular weight and molecular weight distribution, crystallinity, melting point, and glass transition temperature. Except for molecular weight and molecular weight distribution, branching can affect all the other properties mentioned, and branching may be varied (using the same metal complex) using methods described in previously incorporated U.S. Pat. No. 5,880,241. Also in many instances the present iminophosphine complexes give higher polymer yields than other iminophosphine ligands.

The present polymerization process may be a batch, semibatch, continuous, gas phase, solution or liquid slurry etc. type process. For example in a continuous gas phase polymerization process the catalyst system is typically supported on a solid particulate support such as silica or alumina, and fluidized bed-like conditions may be employed. Supportation of metal complexes for polymerization catalysts is known in the art, and such methods for supportation which are known may be used with the present catalysts. Hydrogen or other compounds known to be chain transfer agents may be used for polymer molecular weight control. More than two polymerization catalyst systems may be used with the present catalysts. For example one of the polymerization systems may employ the catalysts described herein, which another polymerization system may be a second system as described herein, another late transition metal polymerization catalyst system, a Ziegler-Natta-type polymerization catalyst system or a metallocene-type polymerization system. More than two such polymerization catalyst systems may be employed. Polymerization processes employing two or more polymerization catalyst systems may produce polyolefin blends which have advantageous properties over single polymers.

In the Examples all the operations related to catalysts or phosphines were carried out under an argon atmosphere. Anhydrous solvents were used in the reactions. Solvents were distilled from drying agents or passed through alumina columns under an Ar or $N_2$ atmosphere. The $^1H$ and $^{31}P$ spectra were recorded using a Bruker® 300 or 400 MHz spectrometer and referenced against residual solvent peaks ($^1H$) or $H_3PO_4$ ($^{31}P$). Branching (measuring methyl groups) per 1000 carbon atoms was determined from $^1H$ spectra. Flash chromatography was performed using 60 Å silica gel (SAI). Room temperature GPC measurements were performed on a Waters Alliance® HPLC Separations Module equipped with a Waters Styragel® HR2, HR4, and HR5 columns in series and a Waters® 2410 Differential Refractometer RI (refractive index) detector relative to polystyrene standards. Samples consisted of ~1 mg polymer in 1 mL of degassed THF. High temperature (135° C.) GPC in 1,2,4-trichlorobenzene using a Waters HPLC equipped with Shodex® columns. A calibration curve was established with polystyrene standards.

The following compounds were made using published methods:

2,4,6-Triisopropylphenyldichlorophosphine: G. M. Whitesides et. al., *J. Am. Chem. Soc.* 1974, 96, 5398.

Mesityldichlorophosphine: D. Seebach et. al. *Helv. Chim. Acta* 1993, 76, 2654.

(cod)PdMeCl: P. W. N. M. van Leeuwen, K. Vrieze et. al., *Inorg. Chem.* 1993, 32, 5769.

The following abbreviations are used:
br—branches
cod—1,4-cyclooctadiene
DME—1,2-dimethoxyethane
GPC—gel permeation chromatography
Me—methyl
Mesityl—2,4,6-trimethylphenyl
MMAO—modified methylaluminoxane
Mn—number average molecular weight
Mw—weight average molecular weight
$NaBArF_4$—sodium tetrakis(3,5-bis(trifluoromethyl)phenyl)borate
PDI—Mw/Mn
PMAO-IP—methyl aluminoxane
RT—room temperature
THF—tetrahydrofuran
TO—turnovers, average number of molecules of ethylene reacted per catalyst molecule per unit time
TON—turnover number (moles olefin consumed/moles catalyst)
TSOH—p-toluenesulfonic acid In the Examples given below structures of the various metal complexes ("C" series) are given below.

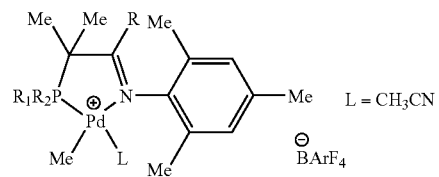

R = H, $R_1$ = 2,4,6-triisopropylphenyl, $R_2$ = Me; C17
R = H, $R_1$ = mesityl, $R_2$ = Me; C18
R = Ph, $R_1$ = mesityl; $R_2$ = Me; C19
R = Ph, $R_1$ = $R_2$ = Me; C20
R =      $R_1$ = $R_2$ = Ph; C21.

EXAMPLE 1

Synthesis of Isobutyraldehyde 2,4,6-Trimethylphenylimine 2,4,6-Trimethylaniline (7.0 mL, 50 mmol, Aldrich) was mixed with isobutyraldehyde (4.5 mL, 50 mmol, Aldrich), methanol (20 mL), and formic acid (1 mL of a 88% aqueous solution, Fisher). The reaction mixture became reddish and was stirred at RT for 4 h. Assay by $^1$H-NMR showed a 2/1 mixture of product/starting materials. Additional isobutyric aldehyde (4 mL, 44 mmol) was added to the reaction mixture and it was stirred for 12 h. At this point assay by $^1$H-NMR showed a 5/1 mixture of product/amine. The solvent and excess aldehyde was evaporated, the residue was distilled at reduced pressure collecting three fractions: 1. 53–56° C./27 Pa, 1/1 mixture of product/amine; 2. 56–59° C., 7/1 product/amine; 3. 59–60° C., pure product (2.3 g, 24.3%). $^1$H NMR (CDCl$_3$) 7.52 (d, 1H; J=4.8 Hz); 6.84 (br s, 2H); 2.70 (d of septets, 1H; J=4.8; 6.9 Hz); 2.26 (s, 3H); 2.05 (s, 6H); 1.22 (d, 6H; J=6.9 Hz).

EXAMPLE 2

Preparation of Catalyst C17

To a solution of isobutyraldehyde 2,4,6-trimethylphenylimine (Example 1, 0.189 g, 1.0 mmol) in diethyl ether (2 mL) was added t-BuLi (0.62 mL of a 1.7M solution in pentane, 1.05 mmol, Aldrich) at –78° C. The solution was stirred for 10 min at –78° C., warmed to RT and stirred for 15 min. The yellow solution of azaenolate was added dropwise to a solution of 2,4,6-triisopropylphenyldichlorophosphine (0.305 g, 1.0 mmol) in THF (3 mL) at –78° C. The mixture was stirred at –78° C. for 10 min, warmed to RT and stirred for additional 30 min. Assay by $^{31}$P-NMR (crude reaction mixture) showed the presence of a single major product (+100.1 ppm). The reaction mixture was recooled to –78° C., MeMgBr (0.34 mL of a 3.1 M solution in ether, 1.05 mmol, Strem) was added in one portion. After warming to RT the mixture was stirred for 12 h. Assay by $^{31}$P-NMR (crude reaction mixture) showed the presence of a single major product (–22.7 ppm) together with traces of unidentified impurity (+85 ppm). Filtration through a pad of silica gel in ethyl ether followed by evaporation afforded a white semi-crystalline material. To the crude ligand was added (cod)PdMeCl (0.135 g, 0.5 mmol) and CH$_2$Cl$_2$ (5 mL). The reaction mixture was stirred for 30 min at RT, the solvent evaporated, and the residue purified by extraction with hexanes (2×10 mL). Product was obtained as a yellowish, hexane-insoluble powder, 0.19 g (32.0%); mixture of two isomers, 8/1 ratio. Major: $^{31}$P{$^1$H} NMR (CD$_2$Cl$_2$): +27.0 ppm (s). Minor: $^{31}$P{$^1$H} NMR (CD$_2$Cl$_2$): +40.3 ppm (s).

To the mixture of the above complex (0.100 g, 0.168 mmol) was added NaBArF$_4$ (0.150 g, 0.168 mmol, Boulder Scientific), dry acetonitrile (2 mL) and CH$_2$Cl$_2$ (2 mL). The reaction was stirred for 12 h at RT and then cannula filtered to remove NaCl. After evaporation C17 was obtained as a yellowish powder, 0.222 g (90.3%); mixture of two isomers, 30/1 ratio. Major: $^{31}$P{$^1$H} NMR (CD$_2$Cl$_2$): +30.8 ppm (s). Minor: $^{31}$P{$^1$H} NMR (CD$_2$Cl$_2$): +28.5 ppm (s).

EXAMPLE 3

Preparation of Catalyst C18

To a solution of isobutyraldehyde 2,4,6-trimethylphenylimine (0.378 g, 2.0 mmol) in ethyl ether (5 mL) was added t-BuLi (1.25 mL of a 1.7M solution in pentane, 2.1 mmol, Aldrich) at –78° C. The solution was stirred for 10 min at –78° C., warmed to RT and stirred for 20 min. The yellow solution of azaenolate was dropwise added to a solution of 2,4,6-trimethylphenyldichlorophosphine (0.37 mL, 2.1 mmol) in THF (5 mL) at –78° C. The mixture was stirred at –78° C. for 10 min, warmed to RT and stirred for additional 30 min. Assay by $^{31}$P-NMR (crude reaction mixture) showed the presence of a single major product (+101.5 ppm). The reaction mixture was recooled to –78° C. and MeMgBr (0.71 mL of a 3.1 M solution in ether, 2.2 mmol, Strem) was added in one portion. After warming to RT the mixture was stirred for 30 min. Assay by $^{31}$P-NMR (crude reaction mixture) showed the presence of a single major product (–18.0 ppm) together with the starting material (+101.5 ppm). The reaction mixture was recooled to –78° C., additional MeMgBr (1 mL, 3.1 mmol) was added. After warming to RT the mixture was stirreu for 12 h. $^{31}$P-NMR (crude reaction mixture) showed the complete consumption of the starting material. TMSCl (0.5 mL) was added to quench the excess MeMgBr, the solution was stirred for 30 min at RT, evaporated and the residue extracted with hexanes (4×10 mL). The hexane in the extracts were evaporated to give the iminophosphine ligand as a yellowish oil. To the crude ligand was added (cod)PdMeCl (0.26 g, 0.98 mmol) and CH$_2$Cl$_2$ (5 mL). The reaction mixture was stirred for 30 min at RT, evaporated, and the residue purified by extraction with hexanes (3×10 mL). Product was obtained as a light yellow, hexane-insoluble powder, 0.37 g (36.3%). $^{31}$P{$^1$H} NMR (CD$_2$Cl$_2$): +31.2 ppm (s).

The synthesis of cationic acetonitrile complex C18 was performed as in the case of C17, using 0.196 mmol of starting materials, reaction time 14 h. Product was obtained as a light yellow foam, 0.24 g (88.8%). $^{31}$P{$^1$H} NMR (CD$_2$Cl$_2$): +34.4 ppm (s).

EXAMPLE 4

Synthesis of Isobutyrophenone 2,4,6-Trimethylphenylimine 2,4,6-Trimethylaniline (16.9 mL, 120 mmol, Aldrich) was mixed with isobutyrophenone (12.0 mL, 80 mmol, Acros) and p-TsOH (1.5 g, 8.0 mmol, Aldrich). The resulting mixture was heated for 10 h at 220° C. in a flask equipped with a Dean-Stark trap. Vacuum distillation afforded two fractions: 1. unreacted starting materials, 40–48° C./40 Pa; 2. product as a yellow oil, 98–108° C./13 Pa (6.2 g, 29.2%). $^1$H NMR (toluene-d$_8$, 353 K) 7.28–6.78 (m, 4H); 6.62 (s, 2H); 2.96 (septet, 1H; J=6.7 Hz); 2.07 (s, 3H); 1.97 (s, 6H); 1.23 (d, 6H; J=6.7 Hz).

EXAMPLE 5

Preparation of Catalyst C19

To a solution of isobutyrophenone 2,4,6-trimethylphenylimine (0.53 g, 2.0 mmol) in ethyl ether (5 mL) was added t-BuLi (1.25 mL of a 1.7 M solution in pentane, 2.1 mmol, Aldrich) at –78° C. The solution was stirred for 10 min at –78° C., warmed to RT, and stirred for 20 minutes. The red-brown solution of azaenolate was added dropwise to a solution of mesityldichlorophosphine (0.37 mL, 2.1 mmol) in THF (5 mL) at –78° C. The mixture was stirred at –78° C. for 10 min, warmed to RT and stirred for an additional 30 min. Assay by $^{31}$P-NMR (crude reaction mixture) showed the presence of a single major product (+103.7 ppm). The reaction mixture was recooled to −78° C. and MeMgBr (1.4 mL of a 3.1 M solution in ether, 4.3 mmol, Strem) was added in one portion. After warming to RT the mixture was stirred for 30 min. Assay by $^{31}$P-NMR (crude reaction mixture) showed the presence of a single major product (−20.3 ppm). TMSCl (0.5 mL) was added to decompose the excess MeMgBr, the solution was stirred for 30 min at RT and evaporated. The residue was extracted with hexanes (4×10 mL). The hexane extracts were evaporated to give crude ligand as a yellow oil. To the crude ligand was added (cod)PdMeCl (0.416 g, 1.57 mmol) and $CH_2Cl_2$ (5 mL). The reaction mixture was stirred for 30 min at RT, evaporated, and the residue purified by extraction with hexanes (3×10 mL). Product was obtained as a white, hexane-insoluble powder, 0.94 g (80.2%). $^{31}P\{^1H\}$ NMR ($CD_2Cl_2$): +41.6 ppm (s).

The synthesis of cationic acetonitrile complex C19 was performed as in the case of C17, using 0.171 mmol of starting materials, reaction time 14 h. Product was obtained as a white powder, 0.228 g (91.6%). $^{31}P\{1H\}$ NMR ($CD_2Cl_2$): +42.2 ppm (s).

EXAMPLE 48

Preparation of Catalyst C20

To a solution of isobutyrophenone 2,4,6-trimethylphenylimine (0.265 g, 1.0 mmol) in ethyl ether (3 mL) was added t-BuLi (0.62 mL of a 1.7 M solution in pentane, 1.05 mmol, Aldrich) at −78° C. The solution was stirred for 10 min at −78° C., warmed to RT and stirred for 30 min. The red-brown solution of azaenolate was added dropwise to a solution of dimethylchlorophosphine (0.083 mL, 1.05 mmol, Strem) in THF (2 mL) at −78° C. The mixture was stirred at −78° C. for 10 min, warmed to RT and stirred for an additional 30 min. Assay by $^{31}$P-NMR (crude reaction mixture) showed the presence of a single major product (−27.9 ppm). The solvent was evaporated from the reaction mixture, the residue extracted with toluene and filtered through a plug Celite® to remove inorganic salts. After evaporation of the solvent crude ligand was obtained as a yellowish oil. To the crude ligand was added (cod)PdMeCl (0.195 g, 0.74 mmol) and $CH_2Cl_2$ (5 mL). The reaction mixture was stirred for 30 min at RT, filtered and evaporated. The residue was purified by flash chromatography on silica gel (3.3×2.3 cm) in $CH_2Cl_2$ followed by ethyl acetate. Solvent was evaporated from fractions containing the product and the residues triturated with ethyl acetate (10 mL) to give product (0.202 g, 41.9%) as a white powder. $^{31}P\{^1H\}$ NMR ($CDCl_3$): +45.6 ppm (s).

The synthesis of the cationic acetonitrile complex C20 was performed as in the case of C17, using 0.166 mmol of starting materials, reaction time 2 h. Product was obtained as a white powder, 0.211 g (94.1%). $^{31}P\{^1H\}$ NMR ($CD_2Cl_2$/toluene-$d_8$ 1/2): +43.0 ppm (s).

EXAMPLE 7

Preparation of Catalyst C21

The synthesis was carried out similarly to that of C20 (Example 6) on a 2 mmol scale using chlorodiphenylphosphine (0.38 mL, 2.1 mmol, Aldrich) instead of chlorodimethylphosphine. Assay by $^{31}$P-NMR (crude reaction mixture) showed the presence of the product (+13.4 ppm). The solvent was evaporated from the reaction mixture, the residue extracted with toluene and filtered through a plug of Celite® to remove inorganic salts. After evaporation of the solvent crude ligand was obtained as a yellowish oil. To the crude ligand was added (cod)PdMeCl (0.270 g, 1.02 mmol) and $CH_2Cl_2$ (5 mL). The reaction mixture was stirred for 12 h at RT. After evaporation the residue was extracted with hexanes (2×10 mL) to give product (0.202 g, 41.9%) as a light yellow, hexane-insoluble powder. $^{31}P\{^1H\}$ NMR ($CD_2Cl_2$): +71.2 ppm (s).

The synthesis of the cationic acetonitrile complex C21 was performed similarly to that of C17, using 0.165 mmol of starting materials, reaction time 12 h. Product was obtained as a white powder, 0.210 g (94.1%). $^{31}P\{^1H\}$ NMR ($CD_2Cl_2$): +71.5 ppm (s).

EXAMPLE 8–11

Oligomerizations of Ethylene Using Catalysts C17–C21

Oligomerizations were carried out in a mechanically stirred 300 mL Parr® reactor equipped with an electric heating mantle controlled by a thermocouple in the reaction mixture. The reactor was charged with toluene (100 mL) and heated for 1 h at 150° C. After cooling to RT the solvent was poured out and the reactor heated under vacuum at 150° C. for 1 h. The reactor was filled with Ar, cooled to RT, pressurized to 200 psi ethylene and vented three times. A solution of the catalyst in 100 mL of the appropriate solvent was added to the reactor via cannula and the reactor heated to the required temperature. If necessary, an activator was added at this time. After that the reactor was pressurized with ethylene and the reaction mixture stirred for the appropriate time. After venting the reaction mixture was worked up in one of three ways:

A. the reaction mixture was evaporated; this method was used for all Pd-catalyzed oligomerizations described below.

B. the reaction mixture was extracted with 10% HCl (occasionally chloroform was added to make the separations better) and evaporated;

C. the reaction mixture was poured into methanol and stirred for 1 h, the precipitate washed with 1:1 mixture of methanol and 10% aqueous HCl, and then with methanol.

Higher molecular weight polymers were dried in vacuum oven at 75° C.

None of the catalysts displayed significant reactivity at RT (2.76 MPa ethylene). Catalyst C20 was unreactive at 80° C. in toluene.

EXAMPLE 8

Oligomerization Using Catalyst C17

C17: 0.01 mmol (15 mg), 2.76 MPa ethylene, 80° C., 3 h.
Toluene solvent: 462 mg oligomers isolated, 550 TO/h, Mn=560, 81 br/1000° C.
Chlorobenzene solvent: 616 mg oligomers isolated, 733 TO/h, Mn=507, 72 br/1000° C.

EXAMPLE 9

Oligomerization Using Catalyst C18

C18: 0.011 mmol (16 mg), 2.76 MPa ethylene, 80° C., toluene.
Three h: 432 mg oligomers isolated, 467 TO/h, Mn=351, 89 br/1000° C.
Fifteen h: 967 mg oligomers isolated, 209 TO/h, Mn=352, 90 br/1000° C.

EXAMPLE 10

Oligomerization Using Catalyst C19

C19: 0.011 mmol (17 mg), 4.76 MPa ethylene, 80° C., 3 h.

Toluene solvent: 56 mg oligomers isolated, 61 TO/h, Mn=662.

Chlorobenzene solvent: 92 mg oligomers isolated, 100 TO/h, Mn=616.

EXAMPLE 11

Oligomerization Using Catalyst C21

C21: 0.01 mmol (15 mg), 400 psi ethylene, 80° C., 3 h.

Chlorobenzene solvent: 110 mg oligomers isolated, 131 TO/h, Mn=307.

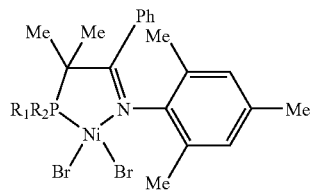

$R_1 = R_2 = Me$; C22
$R_1 = Me$; $R_2 = 2,6$-dimethylphenolato; C23
$R_1 = R_2 = Ph$; C24
$R_1 = Me$, $R_2 = $ mesityl; C25
$R_1 = R_2 = 2$-tolyl; C26

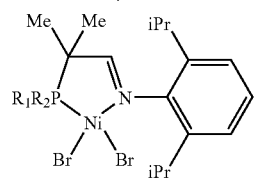

$R_1 = Me$; $R_2 = 2,4,6$-triisopropylphenyl; C27

EXAMPLE 12

Preparation of Catalyst C22

To crude ligand (obtained similarly to C20 using 1 mmol imine) was added NiBr$_2$(DME) (0.240 g, 0.78 mmol) and CH$_2$Cl$_2$ (5 mL). The dark purple solution was stirred for 1 h at RT, the solution was evaporated and the residue washed with hexanes (3×10 mL). A purple solid (0.42 g, 99.0% based on Ni) was obtained.

EXAMPLE 13

Preparation of Catalyst C23

Lithium azaenolate was prepared as in Example 6 using 1 mmol of the imine. The solution of the azaenolate was added to a solution of dichloromethylphosphine (0.094 mL, 1.05 mmol, Strem) in THF (4 mL) at −78° C. The yellow solution was stirred for 10 min at −78° C., warmed to RT and stirred for 30 min. Assay by $^{31}$P-NMR (crude reaction mixture) showed the presence of one major product (+101.7 ppm). Meanwhile, BuLi (0.68 mL, 1.1 mmol, Aldrich) was added to a solution of 2,6-dimethylphenol (0.13 g, 1 mmol, Aldrich) in THF (5 mL) at −78° C. followed by warming to RT. The reaction mixture containing imine-phosphine was recooled to −78° C. and a solution of lithium 2,6-dimethoxyphenolate was added. After stirring for 10 min at −78° C., warming to RT and stirring for additional 2 h, assay by $^{31}$P-NMR (crude reaction mixture) showed the presence of a single major product (+135.4 ppm). The solution was evaporated, the residue extracted with 10 mL toluene, filtered through a pad of Celite® and washed with 3×10 mL toluene. The solvent was evaporated to give crude ligand as a yellow oil. To crude ligand (1/2 of the above material) was added NiBr$_2$(DME) (0.093 g, 0.30 mmol) and CH$_2$Cl$_2$ (5 mL). The dark purple solution was stirred for 1 h at RT, the solution was evaporated and the residue washed with diethyl ether (10 mL) and hexanes (2×10 mL). A purple solid (0.149 g, 88.4% based on Ni) was obtained.

EXAMPLE 14

Preparation of Catalyst C24

Lithium azaenolate was prepared as Example 6 using 2 mmol of the imine. A solution of chlorodiphenylphosphine (0.38 mL, 2.1 mmol, Acros) in THF (1 mL) was added to the solution of the azaenolate at −78° C. The yellow solution was stirred for 10 min at −78° C., warmed to RT and stirred for 1 h. Assay by $^{31}$P-NMR (crude reaction mixture) showed the presence of two major products (+13.5; +19.5 ppm; 5/1) and residual chlorodiphenylphosphine (+88.1 ppm). The solution was evaporated, the residue extracted with hexanes (10 mL), filtered through a pad of Celite® and washed with 3×10 mL hexanes. The solvent was evaporated to give crude ligand as a yellow oil. To crude ligand was added NiBr$_2$(DME) (0.124 g, 0.40 mmol) and CH$_2$Cl$_2$ (5 mL). The dark purple solution was stirred for 1 h at RT, the solution was evaporated and the residue washed with ethyl ether (2×20 mL) and hexanes (3×10 mL). A dark red-brown solid (0.26 g, 97.3% based on Ni) was obtained. No signal in the $^{31}$P spectrum was observed; $^1$H NMR (CD$_2$Cl$_2$) 8.71 (br s, 4H); 7.80 (s, 2H); 7.39–7.18 (m, 7H); 7.10 (d, 2H; J=7.3 Hz); 6.39 (t, 2H; J=7.3 Hz); 4.76 (s, 3H); 4.30 (s, 6H); 2.53 (s, 6H).

EXAMPLE 15

Preparation of Catalyst C25

Lithium azaenolate was prepared as in Example 6 using 2 mmol of the imine. The red-brown solution of azaenolate was added dropwise to a solution of dichloromethylphosphine (0.2 mL, 2.2 mmol, Strem) in THF (5 mL) at −78° C. The mixture was stirred at −78° C. for 10 min, warmed to RT and stirred for additional 30 min. Assay by $^{31}$P-NMR (crude reaction mixture) showed the presence of a single major product (+101.5 ppm) in addition to starting materials (+194.5; +190.7 ppm). The solvent was evaporated under vacuum to remove excess MePCl$_2$ and THF (5 mL) was added. The reaction mixture was recooled to −78° C. and mesitylmagnesium bromide (4 mL of a 1 M solution in ether, 4 mmol, Aldrich) was added in one portion. After warming to RT the mixture was stirred for 30 min. Assay by $^{31}$P-NMR (crude reaction mixture) showed the presence of a single major product (−20.3 ppm). Acetic acid (3 drops) was added to decompose the excess Grignard reagent and the solvent was removed under vacuum. The residue was dissolved in CH$_2$Cl$_2$ and filtered through a 3×2.2 cm plug of silica gel under Ar, eluting with CH$_2$Cl$_2$ (30 mL) followed by ethyl ether (20 mL). The solvent was evaporated to give crude ligand as a yellow oil. To the crude ligand was added NiBr$_2$(DME) (0.124 g, 0.40 mmol) and CH$_2$Cl$_2$ (10 mL). The dark purple solution was stirred for 1 h at RT, solution was evaporated and the residue washed with diethyl ether (2×20 mL) and hexanes (20 mL). A violet solid (0.26 g, 100% based on Ni) was obtained. No signal in $^{31}$P spectrum was observed; $^1$H NMR (CD$_2$Cl$_2$) 7.29–7.14 (m, 5H); 6.97 (br d, 1H; J=6.0); 6.82 (br d, 1H; J=6.0); 6.75 (s, 1H); 6.82 (S, 1H); 4.65 (br s, 6H); 3.18 (s, 3H); 3.16 (s, 3H); 2.37 (s, 3H); 2.26 (s, 3H); 2.22 (s, 3H); 1.37 (s, 6H).

EXAMPLE 16

Synthesis of Isobutyraldehyde 2,6-Diisopropylphenylimine 2,6-Diisopropylaniline (9.4 mL, 50 mmol, Aldrich) was mixed with isobutyric aldehyde (9.1 mL, 100 mmol, Aldrich), p-toluenesulfonic acid (0.48 g, 2.5 mmol, Aldrich), chloroform (50 mL) and MgSO$_4$ (12 g, 100 mmol). The mixture was stirred for 2 h at RT. Assay by $^1$H-NMR (crude reaction mixture) showed the presence of product and starting material (8/1 ratio). The reaction mixture was filtered, the precipitate washed with chloroform (50 mL), and 5 Å molecular sieves were added. After stirring for 20 h at RT the solution was filtered, the molecular sieves were washed with chloroform (2×50 mL), the solvent was evaporated, and the residue distilled at reduced pressure. After a few drops of forerun (67–76° C./27 Pa) product was collected at 76–77° C./27 Pa as a colorless oil, 8.66 g (74.8%). $^1$H NMR (CDCl$_3$) 7.60 (d, 1H; J=4.8 Hz); 7.20–7.05 (m, 3H); 3.00 (septet, 2H; J=6.8 Hz); 2.78 (d of septets, 1H; J=4.8; 6.7 Hz); 1.33 (d, 6H; J=6.7 Hz); 1.23 (d, 12H; J=6.8 Hz).

EXAMPLE 17

Synthesis of Bis(2-methylphenyl)chloro- and bromophosphines

A solution of ZnCl$_2$ (7.0 g, 101 mmol, Aldrich; fused under vacuum) in THF (70 mL) was added to o-tolylmagnesium bromide (50 mL of a 2.0 M solution in ethyl ether; 100 mmol, Aldrich) at 0° C. The solution was warmed to RT and added dropwise to a solution of PCl$_3$ (4.3 mL, 49 mmol, Aldrich) in THF (30 mL) at −78° C. The solution was stirred for 10 min at −78° C., warmed to RT and stirred for 30 min. Assay by $^{31}$P-NMR (crude reaction mixture) showed the presence of a mixture of bis(2-methylphenyl)chlorophosphine and bis(2-methylphenyl)bromophosphine (+74.1; +66.3 ppm, 1/0.75 ratio). The solvent was evaporated, hexanes (200 mL) added to the residue and the solution was filtered through Celite® followed by washing of the precipitate with toluene (50 mL) and hexanes (4×50 mL). Evaporation of the solvent followed by distillation under reduced pressure afforded the product (bp 125–131° C./27 Pa, 8.3 g, 62.0%) as a yellowish solid, 1/0.75 ratio of P-Cl/P—Br.

EXAMPLE 18

Preparation of Catalyst C26

Lithium azaenolate was prepared as in Example 6 using 2 mmol of the imine. The red-brown solution of azaenolate was dropwise added to a solution of bis(2-methylphenyl) chlorophosphine (0.56 g, 2.1 mmol; 1/0.75 R$_2$PCl/R$_2$PBr) in THF (5 mL) at −78° C. The mixture was stirred at −78° C. for 30 min, warmed to RT and stirred for additional 30 min. Assay by $^{31}$P NMR (crude reaction mixture) showed the presence of a major product (−11.5 ppm) in addition to several impurities. The solvent was evaporated under reduced pressure. The residue was dissolved in CH$_2$Cl$_2$ and filtered through a 3×2.2 cm plug of silica gel under Ar, eluting with toluene (30 mL) followed by CH$_2$Cl$_2$ (20 mL). The solvent was evaporated to give crude ligand as a yellow oil. To crude ligand was added NiBr$_2$(DME) (0.123 g, 0.4 mmol) and CH$_2$Cl$_2$ (7 mL). The dark brown-violet solution was stirred for 2.5 h at RT, solution was evaporated and the residue washed with ethyl ether (3×10 mL) and hexanes (10 mL). A brown solid (0.196 g, 70.4% based on Ni) was obtained.

EXAMPLE 19

Preparation of Catalyst C27

Cyclohexylmagnesium bromide (1.05 mL of a 2.0 M solution in ethyl ether, 2.1 mmol, Aldrich) was added to a solution of isobutyraldehyde 2,6-diisopropylphenylimine (0.462 g, 2.0 mmol) in THF (5 mL) at −78° C. The yellowish solution was warmed to RT, stirred for 1 h and then added to a solution of dichloromethylphosphine (0.19 mL, 2.1 mmol, Strem) in THF (5 mL) at −78° C. The solution was stirred for 10 min at −78° C., warmed to RT and stirred for 30 min. Assay by $^{31}$P-NMR (crude reaction mixture) showed the presence of a single major product (+110.4 ppm). The solution of 2,4,6-triisopropylphenyllithium was prepared by addition of BuLi (1.6 mL of a 1.6 M solution in hexanes, 2.6 mmol, Aldrich) to a solution of 1-bromo-2,4, 6-triisopropylbenzene (0.63 mL, 2.5 mmol, Lancaster) in THF (8 mL) at −78° C. followed by stirring for 2 h. The solution of arylLi thus formed was added to the solution of chlorophosphine keeping both flasks at −78° C. The solution was stirred for 20 min at −78° C., warmed to RT and stirred for 30 min. Assay by $^{31}$P-NMR (crude reaction mixture) showed the presence of a single major product (−37.9 ppm). The solution was evaporated and CH$_2$Cl$_2$ (10 mL) was added to the residue. Filtration through a 2.2×2 cm plug of silica gel using CH$_2$Cl$_2$ (20 mL) and then ethyl ether (10 mL) as an eluent followed by evaporation of the solvent afforded crude product as a yellowish oil. To the crude ligand was added NiBr$_2$(DME) (0.124 g, 0.40 mmol) and CH$_2$Cl$_2$ (10 mL). The red-brown solution was stirred for 1 h at RT, solution was evaporated and the residue washed with diethyl ether (3×20 mL) and hexanes (20 mL). A brown, insoluble solid (0.310 g, 107% based on Ni) was obtained.

EXAMPLES 20–41

Ethylene Dimerizations and Polymerizations Using Catalysts C22–C27

Reactions were carried out according to the general method used with in Examples 8–11. Reactions using 200 mL solvent were carried out in a 600 mL Parr® reactor equipped with water cooling and an electric heating mantle controlled by a thermocouple in the reaction mixture.

EXAMPLE 20

Dimerization Using Catalyst C22

C22 0.0046 mmol (2.5 mg), 2.76 MPa ethylene, ethylaluminum dichloride activator (1 mL of a 1.8 M solution in toluene, 1.8 mmol, Aldrich), 100 mL chlorobenzene, 19–26° C. After pressurizing the reactor to 1.03–1.38 MPa with ethylene the temperature was regulated by occasional cooling of the reaction with −78° C. bath (dry ice-acetone). After 20 min the reactor was vented. Assay by $^1$H-NMR showed that 0.8 mol butenes (350,000 TO; 1,050,000 TO/h) were produced.

EXAMPLE 21

Dimerization Using Catalyst C22

C22 0.018 mmol (10 mg), 2.76 MPa ethylene, diethylaluminum chloride activator (3 mL of a 1.8 M solution in toluene, 5.4 mmol, Aldrich), 100 mL chlorobenzene, 35° C. After pressurizing the reactor to 2.76 MPa the temperature was regulated by occasional cooling of the reactor with a wet ice bath. After 30 min the reactor was vented. Assay by $^1$H-NMR showed that mostly butenes were produced.

EXAMPLE 22

Polymerization and Dimerization Using Catalyst C22

C22 0.018 mmol (10 mg), 2.76 MPa ethylene, PMAO-IP activator (3 mL of a 13.5 wt % Al solution in toluene, 13.5 mmol, Akzo-Nobel), 100 mL chlorobenzene, 35° C. After pressurizing the reactor to 2.76 MPa the temperature was regulated by occasional cooling of the reactor with a wet ice bath. After 1 h the reactor was vented. Assay by $^1$H-NMR showed that a mixture of butenes and polymer was produced.

EXAMPLE 23

Polymerization Using Catalyst C22

C22 0.018 mmol (10 mg), 2.76 MPa, MMAO-3A activator (3 mL of a 6.8 wt % Al solution in heptane, 6.6 mmol, Akzo-Nobel), 100 mL chlorobenzene, 31–35° C. After pressurizing the reactor to 2.76 MPa the temperature was regulated by occasional cooling of the reactor with a wet ice bath. After 1 h the reactor was vented. Assay by $^1$H-NMR showed that polymer was produced. Polymer was isolated according to method B. A waxy polymer was obtained, 6.8 g (13,500 TO/h, 65 br/1000 C, Mn=2400 (NMR); 5400 (GPC); Mw=9400; PDI=1.74).

EXAMPLE 24

Polymerization Using Catalyst C22

C22 0.018 mmol (10 mg), 2.76 MPa ethylene, MMAO-3A activator (3 mL of a 6.8 wt % Al solution in heptane, 6.6 mmol, Akzo-Nobel), 100 mL chlorobenzene, 31–35° C. After pressurizing the reactor to 2.76 MPa the temperature was regulated by occasional cooling of the reactor with a wet ice bath. After 5 h the reactor was vented. Assay by $^1$H-NMR showed that polymer was produced. Polymer was isolated according to method B. A waxy polymer was obtained, 18.0 g (7100 TO/h, 66 br/1000 C, Mn=2800 (NMR); 6200 (GPC); Mw=10,900; PDI=1.77).

EXAMPLE 25

Polymerization Using Catalyst C23

C23 (0.01 mmol, 6.5 mg) catalyst, 2.76 MPa ethylene, MMAO-3A activator (3 mL of a 6.8 wt % Al solution in heptane, 6.6 mmol, Akzo-Nobel), 100 mL chlorobenzene, 30° C. After 1 h the reactor was vented. Assay by $^1$H-NMR showed that a small amount of polymer was produced.

EXAMPLE 26

Polymerization Using Catalyst C25

C25 0.01 mmol (6.5 mg), 400 psi ethylene, MMAO-3A activator (3 mL of a 6.8 wt % Al solution in heptane, 6.6 mmol, Akzo-Nobel), 100 mL chlorobenzene, 60° C. After 30 min the reactor was vented. Assay by $^1$H-NMR showed that polymer was produced. Polymer was isolated according to method B. White, sticky powder was obtained, 0.239 g (1700 TO/h, 57 br/1000° C., Mn=5500 (NMR)).

EXAMPLE 27

Dimerization Using Catalyst C27

C27 0.01 mmol (7.0 mg), 1.38 MPa ethylene, MMAO-3A activator (3 mL of a 6.8 wt % Al solution in heptane, 6.6 mmol, Akzo-Nobel), 100 mL chlorobenzene. After pressurizing the reactor to 1.38 MPa the reactor was cooled with a wet ice bath. Temperature rose to 63° C., then dropped to 50° C. After 10 min the reactor was vented. Assay by $^1$H-NMR showed that mostly butenes were produced.

EXAMPLE 28

Polymerization Using Catalyst C24

C24 0.005 mmol (3.3 mg), 2.76 MPa ethylene, MMAO-3A activator (1.5 mL of a 6.8 wt % Al solution in heptane, 3.3 mmol, Akzo-Nobel), 29° C., 200 mL chlorobenzene. After 1 h the reactor was vented. Assay by $^1$H-NMR showed that polymer was produced. Polymer was isolated according to method C. After drying an elastic, clear polymer was obtained, 2.5 g (17,800 TO/h, 56 br/1000 C).

EXAMPLE 29

Polymerization Using Catalyst C24

C24 0.01 mmol (6.6 mg), 2.76 MPa ethylene, MMAO-3A activator (3 mL of a 6.8 wt % Al solution in heptane, 6.6 mmol, Akzo-Nobel), 29° C., 200 mL chlorobenzene. After 1 h the reactor was vented. A white, elastic mass (solvent completely absorbed by polymer) filled the reactor. Assay by $^1$H-NMR showed that polymer was produced. Polymer was isolated according to method C. After drying an elastic, clear polymer was obtained, 8.36 g (29,900 TO/h, 61 br/1000 C, Mn=70,600 (GPC); Mw=133,900; PDI=1.90).

EXAMPLE 30

Polymerization Using Catalyst C24

C24 0.005 mmol (3.3 mg) catalyst, 2.76 MPa ethylene, MMAO-3A activator (4 mL of a 6.8 wt % Al solution in heptane, 8.8 mmol, Akzo-Nobel), 29° C., 200 mL chlorobenzene. After 1 h the reactor was vented. Assay by $^1$H-NMR showed that polymer was produced. Polymer was isolated according to method C. After drying an elastic, clear polymer was obtained, 4.1 g (29,300 TO/h, 62 br/1000 C, Mn=71,600 (GPC); Mw=133,100; PDI=1.86). No significant amount of lower molecular weight material was detected in the methanol used for precipitation.

EXAMPLE 31

Polymerization Using Catalyst C24

C24 0.005 mmol (3.3 mg), 2.76 MPa ethylene, MMAO-3A activator (4 mL of a 6.8 wt % Al solution in heptane, 8.8 mmol, Akzo-Nobel), 29° C., 200 mL chlorobenzene. After 3 h the reactor was vented. A white, elastic mass (solvent completely absorbed by polymer) filled the reactor. Assay by $^1$H-NMR showed that polymer was produced. Polymer was isolated according to method C. After drying an elastic, clear polymer was obtained, 10.0 g (23,800 TO/h, 64 br/1000° C., Mn=75,100 (GPC); Mw=140,100; PDI=1.87; Tm=64.3° C.).

EXAMPLE 32

Polymerization Using Catalyst C24

C24 0.005 mmol (3.3 mg), 2.76 MPa ethylene, MMAO-3A activator (4 mL of a 6.8 wt % Al solution in heptane, 8.8 mmol, Akzo-Nobel), 29° C., 200 mL chlorobenzene. After 5 min the reactor was vented. Assay by $^1$H-NMR showed that polymer was produced. Polymer was isolated according to method B. After drying an elastic, clear polymer was obtained, 0.59 g (63 br/1000° C., Mn=37,300 (GPC); Mw=68,000; PDI=1.83).

EXAMPLE 33

Polymerization Using Catalyst C24

C24 0.005 mmol (3.3 mg), 2.76 MPa ethylene, MMAO-3A activator (4 mL of a 6.8 wt % Al solution in heptane, 8.8 mmol, Akzo-Nobel), 60° C., 200 mL chlorobenzene. After 30 min the reactor was vented. Assay by $^1$H-NMR showed that polymer was produced. Polymer was isolated according to method B. After drying an elastic, clear polymer was obtained, 2.39 g (34,100 TO/h, 69 br/1000° C., Mn=42,200 (GPC); Mw=63,600; PDI=1.51).

EXAMPLE 34

Polymerization Using Catalyst C24

C24 0.005 mmol (3.3 mg), 2.76 MPa ethylene, MMAO-3A activator (4 mL of a 6.8 wt % Al solution in heptane, 8.8 mmol, Akzo-Nobel), 60° C., 200 mL chlorobenzene. After 90 min the reactor was vented. Assay by $^1$H-NMR showed that polymer was produced. Polymer was isolated according to method C. After drying an elastic, clear polymer was obtained, 6.61 g (31,500 TO/h, 70 br/1000° C., Mn=47,300 (GPC); Mw=67,600; PDI=1.43).

EXAMPLE 35

Polymerization Using Catalyst C24

C24 0.005 mmol (3.3 mg), 2.76 MPa ethylene, MMAO-3A activator (4 mL of a 6.8 wt % Al solution in heptane, 8.8 mmol, Akzo-Nobel), 80° C., 200 mL chlorobenzene. After 30 min the reactor was vented. Assay by $^1$H-NMR showed that polymer was produced. Polymer was isolated according to method B. After drying waxy polymer was obtained, 2.63 g (37,600 TO/h, 71 br/1000° C., Mn=30,300 (GPC); Mw=46,300; PDI=1.53).

EXAMPLE 36

Polymerization Using Catalyst C24

C24 0.005 mmol (3.3 mg), 2.76 MPa ethylene, MMAO-3A activator (4 mL of a 6.8 wt % Al solution in heptane, 8.8 mmol, Akzo-Nobel), 80° C., 200 mL chlorobenzene. After 90 min the reactor was vented. Assay by $^1$H-NMR showed that polymer was produced. Polymer was isolated according to method B. After drying waxy polymer was obtained, 4.42 g (21,000 TO/h, 74 br/1000° C., Mn=28,200 (GPC); Mw=45,500; PDI=1.61).

EXAMPLE 37

Polymerization Using Catalyst C24

C24 0.005 mmol (3.3 mg), 2.76 MPa ethylene, tetraethyldialumoxane activator (8.8 mL of a 1.0 solution in toluene, 8.8 mmol, Akzo-Nobel), 29° C., 200 mL chlorobenzene. After 1 h the reactor was vented. Assay by $^1$H-NMR showed that polymer was produced. Polymer was isolated according to method C. After drying an elastic, clear polymer was obtained, 2.1 g (15,000 TO/h, 63 br/1000° C.).

EXAMPLE 38

Polymerization Using Catalyst C24

C24 0.005 mmol (3.3 mg), 100 psi ethylene, MMAO-3A activator (4 mL of a 6.8 wt % Al solution in heptane, 8.8 mmol, Akzo-Nobel), 29° C., 200 mL chlorobenzene. After 60 min the reactor wzs vented. Assay by $^1$H-NMR showed that polymer was produced. Polymer was isolated according to method C. After drying elastic, clear polymer was obtained, 1.98 g (14,100 TO/h, 65 br/1000° C.).

EXAMPLE 39

Dimerization of 1-Octene Using Catalyst C24

C24 (10 mg, 0.015 mmol) was suspended in a mixture of chlorobenzene (10 mL) and 1-octene (20 mL). The mixture was heated to 60° C. and MMAO-3A activator (10 mL of a 6.8 wt % Al solution in heptane, 22 mmol) was added resulting in immediate color change from red-brown to yellow. The mixture was stirred at 60° C. for 3 h, then cooled to 0° C. and quenched with methanol followed by 10% aq. HCl. The organic layer was separated and the volatiles were evaporated. A colorless oil was obtained, 2.24 g (444 TO/h, Mn=242, 68 br/1000° C.; average formula $C_{17}H_{34}$).

EXAMPLE 40

Polymerization Using Catalyst C26

C26 0.01 mmol (7 mg), 2.76 MPa ethylene, MMAO-3A activator (3 mL of a 6.8 wt % Al solution in heptane, 6.6 mmol, Akzo-Nobel), 60° C., 100 mL chlorobenzene. After 35 min the reactor was vented. Assay by $^1$H-NMR showed that polymer was produced. Polymer was isolated according to method B. After drying waxy polymer was obtained, 7.38 g (45,200 TO/h, 71 br/1000° C., Mn=27,500 (GPC); Mw=40,700; PDI=1.48).

EXAMPLE 41

Polymerization Using Catalyst C26

C26 0.01 mmol (7 mg) catalyst, 2.76 MPa ethylene, MMAO-3A activator (8 mL of a 6.8 wt % Al solution in heptane, 17.6 mmol, Akzo-Nobel), 29° C., 200 mL chlorobenzene. After 70 min the reactor was vented. Assay by $^1$H-NMR showed that polymer was produced. Polymer was isolated according to method B. After drying elastic, clear polymer was obtained, 6.33 g (19,400 TO/h, 67 br/1000° C., Mn=41,000 (GPC); Mw=74,900; PDI=1.84).

COMPARATIVE EXAMPLE A

Preparation of Propiophenone 2,4,6-Trimethylphenylimine (17)

2,4,6-Trimethylaniline (11.5 mL, 82 mmol, Aldrich) was mixed with propiophenone (10 mL, 74.5 mmol, Aldrich) and TSOH (1.4 g, 7.3 mmol, Aldrich). The resulting mixture was heated for 2 h at 200° C. under a weak stream of Ar to remove formed $H_2O$. After cooling to RT the reaction mixture was poured into hexanes (100 mL), filtered, and the precipitate washed with additional hexanes (2×100 mL) followed by the evaporation of the filtrate. The residue was filtered through a 9×4.1 cm plug of silica gel in hexanes/ether 10/1 (300 mL collected). After evaporation of the solvent the unreacted starting materials were distilled off under vacuum (45–50° C./53 Pa). The residue was crystallized from methanol at −30° C. Product was isolated as large orange-yellow crystals, 4.8 g, (25.6%). $^1$H NMR (CDCl$_3$) 8.00–7.94 (m, 2H); 7.51–7.45 (m, 3H); 6.89 (s, 2H); 2.50 (q, 2H; J=7.7 Hz); 2.31 (s, 3H); 2.04 (s, 6H); 0.98 (t, 3H; J=7.7 Hz). $^{13}$C NMR (CDCl$_3$): 170.8, 146.4, 138.2, 131.9, 130.3, 128.7, 128.6, 127.7, 125.6, 23.9, 20.9, 18.2, 11.6. Anal. Calcd for $C_{18}H_{21}N$: C, 86.00; H, 8.42; N, 5.57. Found: C, 85.79; H, 8.41; N, 5.56.

COMPARATIVE EXAMPLE B

Preparation of Catalyst C28

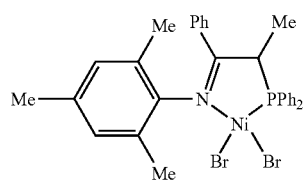

C28

To a solution of di-1-propylamine (0.17 mL, 1.2 mmol, Aldrich) in diethyl ether (5 mL) was added n-BuLi (0.7 mL of a 1.6 M solution in is hexanes, 1.1 mmol, Aldrich) at 0° C., to form LDA. The reaction mixture was stirred at RT for 10 min. The solution of LDA was added to a solution of 17 (0.251 g, 1.0 mmol) in diethyl ether (5 mL) at −78° C. The solution was stirred at −78° C. for 20 min, warmed to RT and stirred for 1 h. After recooling to −78° C. Ph$_2$PCl (0.25 mL, 1.4 mmol, Acros) was added to the solution of the azaenolate at −78° C. The yellow solution was stirred for 15 min at −78° C., warmed to RT and stirred for an additional hour. Assay by $^{31}$P-NMR (crude reaction mixture) showed the presence of one major product (−1.3 ppm) and residual chlorodiphenylphosphine (+83.1 ppm). The residue was filtered through a 3×2.2 cm pad of silica gel in diethyl ether (40 mL) followed by THF (20 mL). The solvent was evaporated to give crude ligand as a yellow oil. To crude ligand was added NiBr$_2$(DME) (0.155 g, 0.5 mmol) and CH$_2$Cl$_2$ (5 mL). The dark purple-brown solution was stirred for 2 h at RT, solution was evaporated and the residue washed with diethyl ether (2×20 mL) and hexanes (3×10 mL). A gray-brown solid (0.263 g, 80.4% based on Ni) was obtained. Anal. Calcd for $C_{30}H_{30}Br_2NNiP$: C, 55.09; H, 4.62; N, 2.14. Found: C, 55.36; H, 4.72; N, 2.08.

COMPARATIVE EXAMPLE C

Ethylene Polymerization Using Catalyst C28

C28 (0.005 mmol, 3.3 mg) catalyst, 2.76 MPa ethylene, MMAO-3A activator (4 mL of a 6.8 wt % Al solution in heptane, 8.8 mmol, Akzo-Nobel), 60° C., 200 mL chlorobenzene. After 1.5 h the reactor was vented. Assay by $^1$H-NMR showed that polymer was produced. Polymer was isolated according to method B. After drying a viscous oil was obtained, 7.0 g (94 br/1000° C., Mn=1160 (GPC); Mw=2440; PDI=2.11). A small amount of polymer was not soluble in the reaction mixture and was separated before the workup, m=0.1 g (89 br/1000° C., Mn=1768; Mw=2970; PDI=1.68). TOF=34,000 TO/h. Comparison of this result with that of Example 34 shows that the complex containing a ligand derived from a nonenolizable ketone as in Example 34 yields a much higher molecular weight polymer than the complex of this comparative example whose ligand is derived from an enolizable ketone.

What is claimed is:
1. A process for the polymerization of olefins, comprising, using a polymerization catalyst system comprising a Ni, Pd, Fe or Co complex of a ligand of the formula:

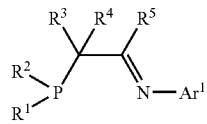

FORMULA (I)

wherein:
Ar$^1$ is aryl or substituted aryl;
R$^1$ is hydrocarbyl, substituted hydrocarbyl, hydrocarbyloxy, or substituted hydrocarbyloxy;
R$^2$ hydrocarbyl or substituted hydrocarbyl;
R$^3$ and R$^4$ are each hydrocarbyl or substituted hydrocarbyl, or R$^3$ and R$^4$ taken together form a ring; and
R$^5$ is hydrocarbyl or substituted hydrocarbyl.

2. The process as recited in claim 1 wherein only 1 molecule of said ligand is coordinated to an atom of said transition metal.

3. The process as recited in claim 2 which is carried out at a temperature of about −100° C. to about +200° C.

4. The process as recited in claim 3 wherein said olefin is ethylene alone.

5. The process as recited in claim 4 wherein $Ar^1$, is phenyl or substituted phenyl.

6. The process as recited in claim 5 wherein said transition metal is Ni.

7. The process as recited in claim 6 wherein:
   $R^1$ is alkyl, substituted alkyl, aryl, substituted aryl, aryloxy, or substituted aryloxy;
   $R^2$ is alkyl, substituted alkyl, aryl or substituted aryl;
   $R^3$ and $R^4$ are each independently alkyl or substituted alkyl; and
   $R^5$ is hydrogen, aryl, substituted aryl, alkyl or substituted alkyl.

8. The process as recited in claim 3 wherein said transition metal is Pd or Ni.

9. A compound of the formula

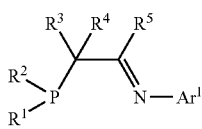

FORMULA (I)

wherein:
   $Ar^1$ is aryl or substituted aryl;
   $R^1$ is hydrocarbyl, substituted hydrocarbyl, hydrocarbyloxy, or substituted hydrocarbyloxy;
   $R^2$ hydrocarbyl or substituted hydrocarbyl;
   $R^3$ and $R^4$ are each hydrocarbyl or substituted hydrocarbyl, or $R^3$ and $R^4$ taken together form a ring; and
   $R^5$ is hydrocarbyl or substituted hydrocarbyl.

10. The compound as recited in claim 9 wherein $Ar^1$, is phenyl or substituted phenyl.

11. The compound as recited in claim 10 wherein:
   $R^1$ is alkyl, substituted alkyl, aryl, substituted aryl, aryloxy, or substituted aryloxy;
   $R^2$ is alkyl, substituted alkyl, aryl or substituted aryl;
   $R^3$ and $R^4$ are each independently alkyl or substituted alkyl; and
   $R^5$ is hydrogen, aryl, substituted aryl, alkyl or substituted alkyl.

12. A transition metal complex of a compound of the formula

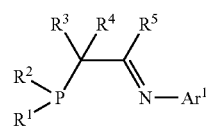

FORMULA (I)

wherein:
   $Ar^1$ is aryl or substituted aryl;
   $R^2$ is hydrocarbyl, substituted hydrocarbyl, hydrocarbyloxy, or substituted hydrocarbyloxy;
   $R^2$ hydrocarbyl or substituted hydrocarbyl;
   $R^3$ and $R^4$ are each hydrocarbyl or substituted hydrocarbyl, or $R^3$ and $R^4$ taken together form a ring; and
   $R^5$ is hydrocarbyl or substituted hydrocarbyl; and
   Wherein $R^5$ is hydrocarbyl or substituted hydrocarbyl, and wherein said transition metal is Fe, Co, Ni or Pd.

13. The complex as recited in claim 12 wherein only 1 molecule of said ligand is coordinated to an atom of said transition metal.

14. The complex as recited in claim 13 wherein said transition metal is Pd or Ni.

15. The complex as recited in claim 14 wherein:
   $Ar^1$ is phenyl or substituted phenyl;
   $R^1$ is alkyl, substituted alkyl, aryl, substituted aryl, aryloxy, or substituted aryloxy;
   $R^2$ is alkyl, substituted alkyl, aryl or substituted aryl;
   $R^3$ and $R^4$ are each independently alkyl or substituted alkyl; and
   $R^5$ is hydrogen, aryl, substituted aryl, alkyl or substituted alkyl.

* * * * *